United States Patent [19]
Daikuzono

[11] Patent Number: 5,865,833
[45] Date of Patent: Feb. 2, 1999

[54] APPARATUS FOR LASER TREATMENT

[75] Inventor: Norio Daikuzono, Cincinnati, Ohio

[73] Assignee: S.L.T. Japan Co., Ltd., Tokyo, Japan

[21] Appl. No.: 977,344

[22] Filed: Nov. 24, 1997

[51] Int. Cl.⁶ ................................................. A61B 17/00
[52] U.S. Cl. ............................................................. 606/14
[58] Field of Search ................................ 606/13, 14, 15, 606/46; 607/105, 115; 604/20, 21

[56] References Cited

U.S. PATENT DOCUMENTS 5,423,807  6/1995  Milder ...................................... 607/105
5,643,197  7/1997  Brucker et al. ............................ 604/20

*Primary Examiner*—George Manuel
*Attorney, Agent, or Firm*—McDermott, Will & Emery

[57] ABSTRACT

The present invention relates to an apparatus for laser treatment for treating the tissue of a human body such as herniated lumbar intervertebral disc by irradiating it with laser light for vaporizing it. The apparatus comprises a hollow needle member which is percutaneously inserted into the target tissue; an optical fiber for transmitting therethrough a laser light from a laser light generator to emit the laser light from the front end thereof; a lead for detecting the temperature of said target tissue and the vicinity thereof; and means for introducing gas which is generated due to vaporization of said irradiated tissue to the outside of the body through the inside of said needle member; and generated gas detecting means for detecting the flow speed or flow rate of the gas which is generated due to the vaporization of said target tissue. The optical fiber and the temperature detecting lead are inserted into said needle member from the base end thereof. The front end of said optical fiber is positioned in said target position. The flow speed or flow rate of the gas is detected by said generated gas detecting means. The temperature of said target tissue and its vicinity is detected based upon a signal of the temperature from said temperature detecting lead. The manner of irradiation with the laser light is controlled based upon the flow speed or flow rate of the detected gas and said temperature.

10 Claims, 10 Drawing Sheets

APPARATUS FOR LASER TREATMENT

DETAILED DESCRIPTION OF THE INVENTION

1. Field of the Invention

The present invention relates to an apparatus for laser treatment for conducting treatment by causing the diseased human tissue such as herniated lumbar intervertebral disc to be vaporized.

2. Prior Art

Lumbar intervertebral discs are disc-shaped tissue located between the vertebrae and comprise a gelatinous nucleus pulposus which is centrally located and is rich in water content and a peripheral annulus fibrosus which consists of fibrous cartilage. Lumbar intervertebral disc herniation is a disease in which the nucleus pulposus is herniated rearward to press the spinal core or the nerve root due to deformation or damages of annulus fibrosus so that nerve symptom is exhibited.

Percutaneous Laser Disc Decompression surgery (PLDD) in which reduction in pressure on the nucleus pulposus is accomplished by irradiating the nucleus pulposus with laser light is effective for treating the herniated lumbar disc. An apparatus which is disclosed in U.S. Ser. No. 08/580,243 filed by the present inventor is applicable for the PLDD surgery using laser light irradiation.

Specifically, vaporization of the nucleus pulposus between lumbar discs is accomplished by irradiating it with laser light emitted from the front end of an optical fiber. A needle member having the optical fiber and a temperature detecting lead disposed therein is inserted into the nucleus pulposus. A gas which is generated by the vaporization of the nucleus pulposus is discharged from the body for removing pains in the waist of a patient.

However it has been found from experiences of various treatments that the apparatus disclosed in U.S. Ser. No. 08/580,243 should be improved in a number of respects.

In other words, a core of the optical fiber in 20 in the prior art is exposed at the front end thereof as shown in FIG. 11. An exposed front end portion 20Y does not have any covering or is not treated on the outer periphery of the core.

Accordingly, since most of the laser light which has been incident into the optical fiber 20 is emitted from only the front end face of the exposed front end portion 20Y, the nucleus pulposus 60*a* is predominantly vaporized in front of the front end portion 20Y. Formation of a solidified layer 60*b* starts with the front end of the needle main body 1 so that it surrounds the vaporized portion 60*a*. As a result of this, the front end portion of the optical fiber 20 is surrounded by the solidified layer 60*b*, so that the solidified layer 60*b* may reach at even the front end of the needle main body 1.

It has been found from experiences of various disease cases that pains may be given to patients as vaporization of the nucleus pulposus advances due to irradiation with laser light since the solidified layer 60*b* is formed from the vaporized portion 60*a* to the front end of the needle main body 1 so that the gas generated by the vaporization can not escape to anywhere, resulting in a gradually increased pressure in the vaporized portion 60*a* and the increased pressure may bias the spinal core or the nerve root.

If a gap is suddenly formed between the end portion 20Y and the solidified layer 60*b* at some point while vaporization continues and the generated gas is discharged from the body through the gap and the needle main body 1, the pains of the patient is then quickly relieved.

On the other hand, the nucleus pulposus may be excessively irradiated with laser light since the irradiation operation relies upon only the operator's experiences in the prior art.

SUMMARY OF THE INVENTION

It is therefor a main object of the present invention to achieve proper treatment by monitoring the irradiation of the target tissue to be treated, such as nucleus pulposus with laser light and vaporization of the nucleus pulposus based upon the flow speed or flow rate of the gas generated due to vaporization.

In accordance with the present invention, there is provided an apparatus for treating the target tissue to be treated by irradiating it with laser light for vaporizing it, characterized in that said apparatus comprises a hollow needle member which is percutaneously inserted into the target tissue;

an optical fiber for transmitting therethrough a laser light from a laser light generator to emit the laser light from the front end thereof;

a lead for detecting the temperature of said target tissue and the vicinity thereof;

means for introducing gas which is generated due to vaporization of said irradiated tissue to the outside of the body through the inside of said needle member; and generated gas detecting means for detecting the flow speed or flow rate of the gas which is generated due to the vaporization of said target tissue, and in that said optical fiber and said temperature detecting lead are inserted into said needle member from the base end thereof, said front end of said optical fiber being positioned in said target tissue;

in that the flow speed or flow rate of the gas is detected by said generated gas detecting means, the temperature of said target tissue and its vicinity being detected based upon a signal of the temperature from said temperature detecting lead; and in that the manner of irradiation with the laser light is controlled based upon the flow speed or flow rate of the detected gas and said temperature.

Said optical fiber may be positioned in such a manner that its front end portion projects beyond the front end of said needle member, said front end portion of said optical fiber being formed on the outer periphery thereof with light scattering means, from which the laser light emits.

Said scattering means may comprise a scattering layer containing finely divided particles having a refractive index less than that of the core, which is formed on the exposed core of the optical fiber at the front end thereof.

A generated gas introducing passage may be provided to communicate with said needle member. Said generated gas introducing passage may be provided with gas detecting means so that it can be determined whether or not vaporization of the tissue occurs and vaporizatino process can be monitored by detecting the generated gas.

The laser treatment apparatus of the present invention is useful as an apparatus for treating the lumbar intervertebral disc herniation in the waist. In this case, the apparatus irradiates the nucleus pulposus with laser light for vaporizing it. Therefore, the apparatus is characterized in that it comprises a hollow needle member which is percutaneously inserted into the uncleus pulposus between the lumbar discs;

an optical fiber for transmitting therethrough a laser light from a laser light generator to emit the laser light from the front end thereof;

a lead for detecting the temperature of said nucleus pulposus and the vicinity thereof;

means for introducing gas which is generated due to vaporization of said nucleus pulposus to the outside of the body through the inside of said needle member; and generated gas detecting means for detecting the flow speed or flow rate of the gas which is generated due to the vaporization of said nucleus pulposus, and in that said optical fiber and said temperature detecting lead are inserted into said needle member from the base end thereof, said front end of said optical fiber being positioned in said nucleus pulposus;

in that the flow speed or flow rate of the gas is detected by said generated gas detecting means, the temperature of said nucleus pulposus and its vicinity being detected based upon a signal of the temperature from said temperature detecting lead; and in that the manner of irradiation with the laser light is controlled based upon the flow speed or flow rate of the detected gas and said temperature.

In this apparatus for treating the lumbar intervertebral disc herniation, the front end of said temperature detecting lead may be positioned in the front end portion of said needle member and said optical fiber may be positioned in such a manner that its front end portion projects beyond the front end of said needle member, said front end portion of said optical fiber being formed on the outer periphery thereof with light scattering means, from which the laser light emits, and said scattering means may comprise a scattering layer containing finely divided particles having a refractive index less than that of the core, which is formed on the exposed core of the optical fiber at the front end thereof.

A generated gas introducing passage may be provided to communicate with said needle member, said generated gas introducing passage being provided with gas detecting means, and means may be provided for automatically controlling the irradiation with laser light based upon said detected flow speed or flow rate of gas and said detected temperature.

In accordance with the present invention, the condition of irradiation of the target tissue, for example, nucleus pulposus with the laser light and the condition of vaporization of the nucleus pulposus can be monitored based on the flow speed or flow rate of the gas which is generated due to vaporization so that appropriate treatment can be achieved. Furthermore, appropriate treatment can be achieved by accepting a signal representing the temperature of the tissue.

DESCRIPTION OF PREFERRED EMBODIMENTS OF THE INVENTION

Figure 1:
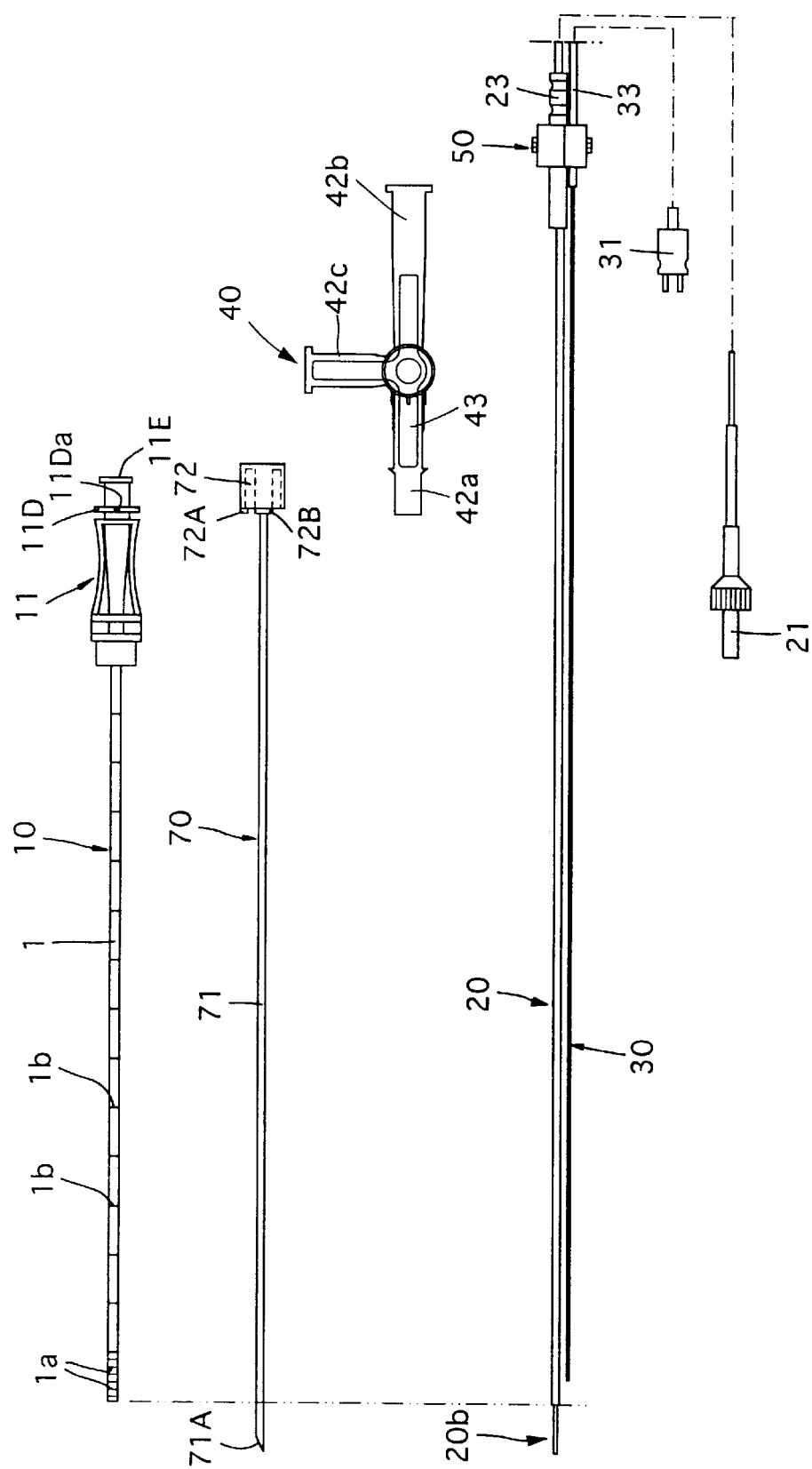
FIG. 1 is a front view showing the whole of main components of the apparatus.
Figure 2:
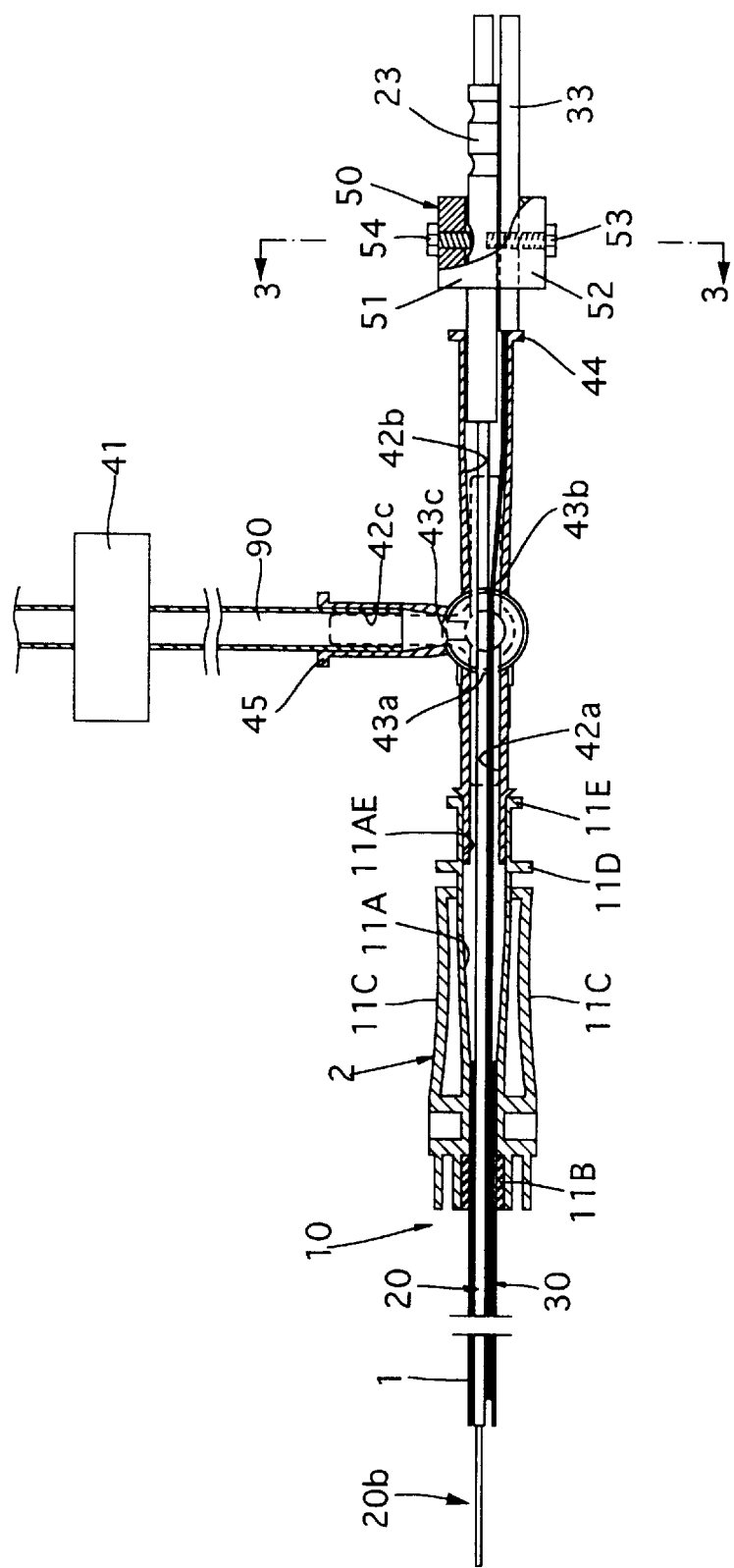
FIG. 2 is a front and partly cutaway view showing the assembly of the main component.

Preferred embodiments of the present invention will be described in detail. FIG. 1 is a front view showing main components of a treating apparatus, which are dissembled. FIG. 2 is longitudinal sectional view showing the parts which have been assembled. The present invention is applied to the treatment of the diseased tissue of the human body by the vaporization thereof. The present invention is applicable to the percutaneous treatment of the liver tumor or brain tumor as well as the percutaneous lumbar intervertebral disc herniation treatment. The present invention will be described by way of the treatment of the lumbar intervertebral disc herniation.

A reference numeral 10 denotes a hollow needle member for inserting a needle main body 1 into the nucleus pulposus of the lumbar intervertebral disc from the outside of a body. The main body of the needle 1 is made a very fine stainless steel tube having a diameter of, for example, 1 mm. The needle main body 1 is secured to the front end of a knob 11 which is a plastic molding. Insertion of the needle main body 1 into the nucleus pulposus 60 together with a drill member 70 is conducted while a surgical operator holds the knob 11 between his or her thumb and middle finger of the right hand and holds the rear end of a drill member 70 with his or her pointing finger.

An optical fiber 20 transmits the laser light from a laser light generator 22 (refer to FIG. 5) to emit it from its front end of the fiber. A lead 30 is provided for detecting the temperature of the nucleus pulposus. A three-directional stopcock 40 is adapted to discharge the gas which is generated by the vaporization of the nucleus pulposus to an apparatus for detecting the amount of the generated gas. The optical fiber 20 and the temperature detecting lead 30 are integrally held by a holder 50 in their intermediate position. The optical fiber 20 is optically linked with a laser light generator 22 through a light emitting terminal 21 (refer to FIG. 5). The temperature detecting lead 30 is connected with a thermometer 32 through a terminal 31 (refer to FIG. 5).

The needle main body which constitutes the needle member 10 is formed at its front or distal end with annular small recesses 1*a* which are spaced in a longitudinal direction thereof in order to prevent the needle main body 1 from escaping while the needle main body 1 is inserted into the nucleus pulposus 60. The needle main body 1 is formed on its outer periphery with spaced indication marks 1*b* made of a material which strongly reflects ultrasonic waves therefrom.

Figure 4:
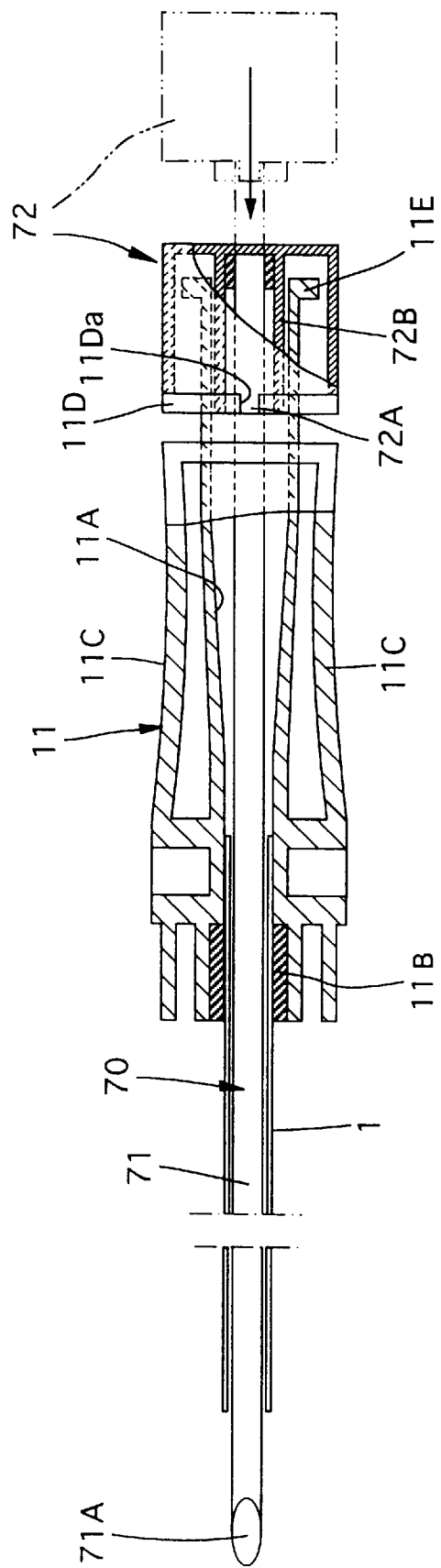
FIG. 4 is a front and partly cutaway view showing that a drill member which is inserted.

As also shown in FIG. 4, the needle main body 1 is inserted at its rear of proximate end into an insertion hole 11A of the knob 11 and is adhesively secured thereto with an adhesive 11. The knob 11 is substantially box-shaped in its intermediate position and has concaved gradually curved faces on the both sides thereof. The insertion hole 11A is tapered from intermediate position toward a receiving hole 11E so that it has a smaller diameter at the front end thereof and a larger diameter at the rear end thereof. The knob 11 is formed with a flange 11D which projects from the rear portion thereof and is also formed with a smaller flange 11E at the rear end thereof. The flange 2D is also formed with an engaging step 11D*a* on a periphery thereof in one position thereof.

Prior to insertion of the optical fiber 20 and the temperature detecting lead 30 into the needle main body 1 of the needle member 10, it is necessary to insert the needle main body 1 into the nucleus pulposus.

At this end, a drill member 30 which is illustrated in detail in FIG. 4 is used for the insertion. The drill member 70 has a drill wire 71 made of stainless steel wire and a depressing member 72 made of plastic molding, which is secured to the rear end of the drill wire 71. The drill wire 71 is obliquely cut at the front or distal end thereof to provide a cut face 71A.

On the other hand, the depressing member 72 is formed at the central portion with a tubular recess 72B into which the rear end portion of the drill wire 71 is adapted and is secured with an adhesive (not shown). The tubular recess 72B has an outer diameter which is slightly smaller than the inner diameter of the receiving hole 11AE. The depressing member 72 is formed on the front end side in a position along the outer periphery thereof with an engaging projection 72A which projects toward the front end side. This projection 72A is adapted to be engaged with the above-mentioned engaging step 11D*a*.

Figure 3:
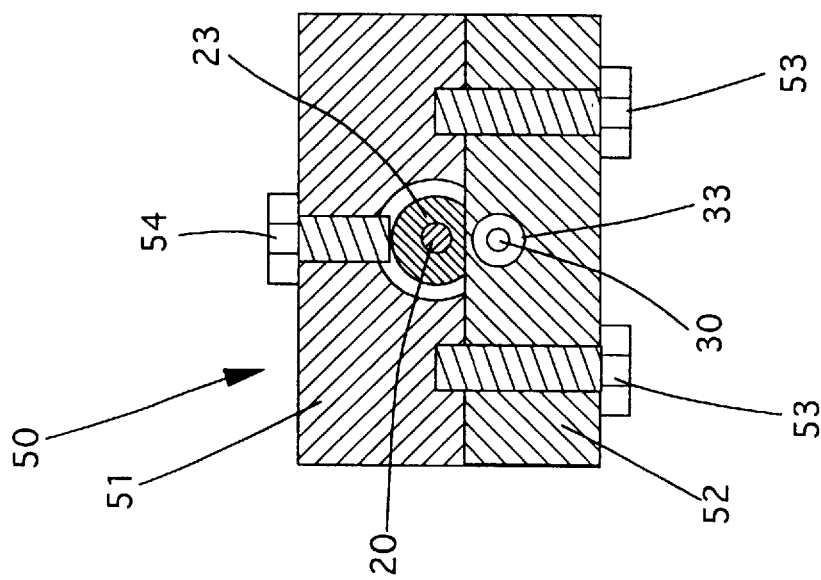
FIG. 3 is an enlarged view taken along the line 3—3 in FIG. 2.

As shown in FIG. 1 to 3, the optical fiber 20 is gripped at the intermediate portion with a grip member 23 of a rigid column which is made of aluminum and is partially cut away in a longitudinal direction so that the fiber 20 is integral with the grip member 23, which is in turn integral with a holder 50. The temperature detecting lead 30 is covered with a protective tube 33 made of flexible plastics excepting its distal end portion thereof. The lead 30 is inserted into a second holder block 52 in a position slightly rear of the front end of the protective tube 33 and is bonded to the block 42 with an adhesive (not shown). The holder 50 comprises a first and second holder blocks 51 and 52, which are secured to each other with screws 53. In order to secure the grip member 23 to the holder 50, a set screw 54 is screwed through the first holder block 51 to firmly secure the outer peripheral recess of the grip member 23.

The three-directional stopcock 40 comprises two insertion portions 42*a*, 42*b*, discharge passage 42*c* and passage adjusting member 43. The passage adjusting member 43 has three through-holes 43*a*, 43*b* and 43*c*. When the stopcock 40 is used in the present invention, it is preset so that all through holes always face toward two insertion portions 42*a*, 42*b* and discharge passage 42*c*, respectively. The insertion portion 42*a* on the front end side thereof is in such a shape that it has inner size thereof decreasing toward the rear end (through hole 43*a*) side from the front end side thereof and the outer size decreasing toward the front end side from the rear side thereof. The insertion portion 42*b* which is opposite to the insertion portion 42*a* is in such a shape that it has an inner and outer sizes increasing from the front end side to the rear end side thereof. The insertion portion 42*b* is formed at the rear end thereof with a flange 44. The discharge passage 42 is in such a shape that it has an inner and outer sizes thereof increasing from the front end thereof (through hole 43*c*) to the rear end side and is formed at the rear end thereof with a flange 45.

Figure 7:
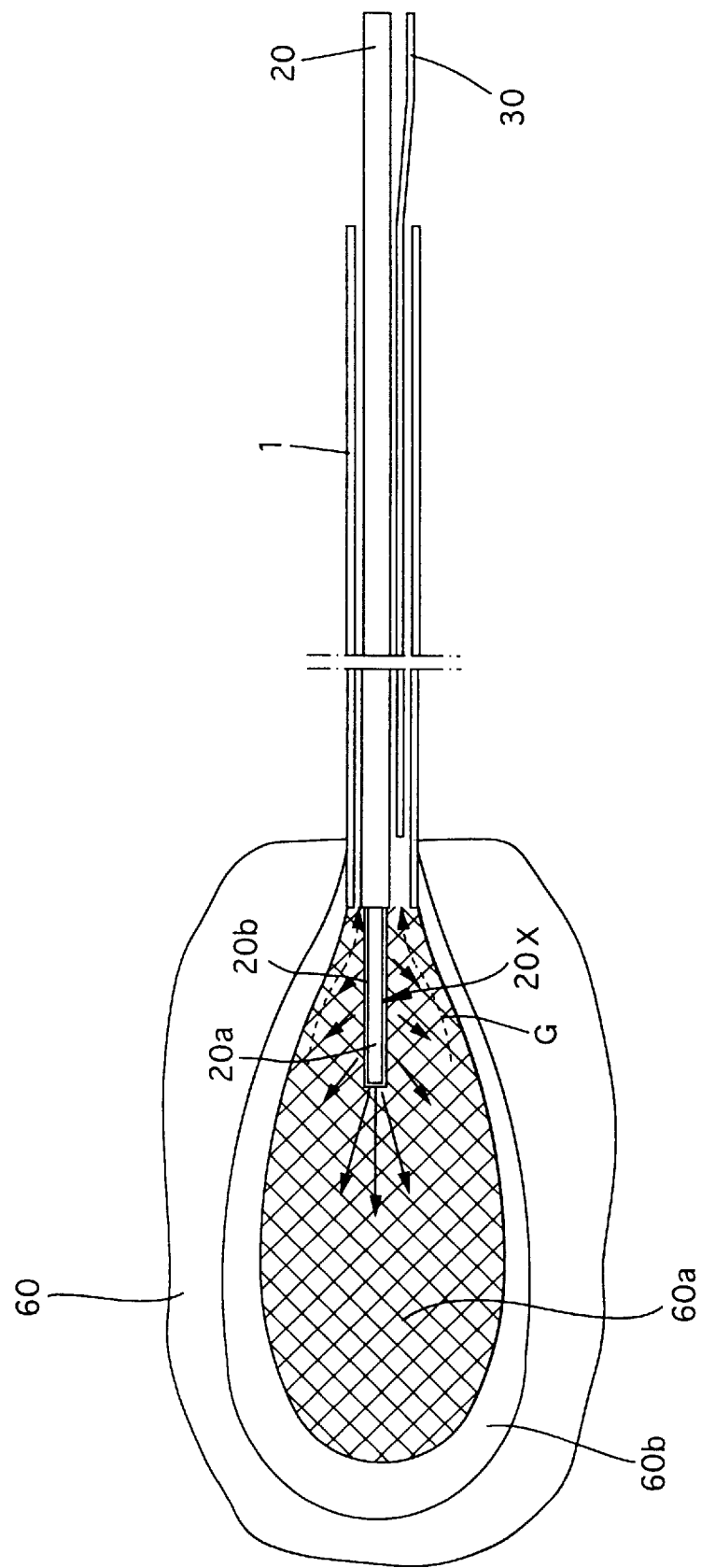
FIG. 7 is a view illustrating the laser light irradiation and the discharge of generated gas.

In the embodiment of the present embodiment, the structure of the front end portion 20X of the optical fiber 20 is improved. As shown in FIG. 7, the optical fiber 20 is positioned in such manner that its front end portion 20X projects beyond the front end of said needle main body 1. At the front end portion 20X, a clad is removed so that a core 20*a* is exposed. Light scattering means comprising a scattering layer 20*b* containing particles having a refractive index less than that of the core 2*a* is provided on the outer periphery of the core 20*a*.

The scattering layer 20*b* has a refractive index less than that of the optical fiber 20 and a high adhesion to the core and can be formed by the steps of dispersing in an organic resin or adhesive composition solvent finely divided particles made of titanium, ceramics, carbon, iron oxide or manganese oxide, applying the dispersion on the outer periphery of the core 20*a*, and then adhering it thereto by drying. The scattering means may include roughed outer peripheral layer on the core 20*a* as well as the scattering layer 20*b*.

Figure 5:
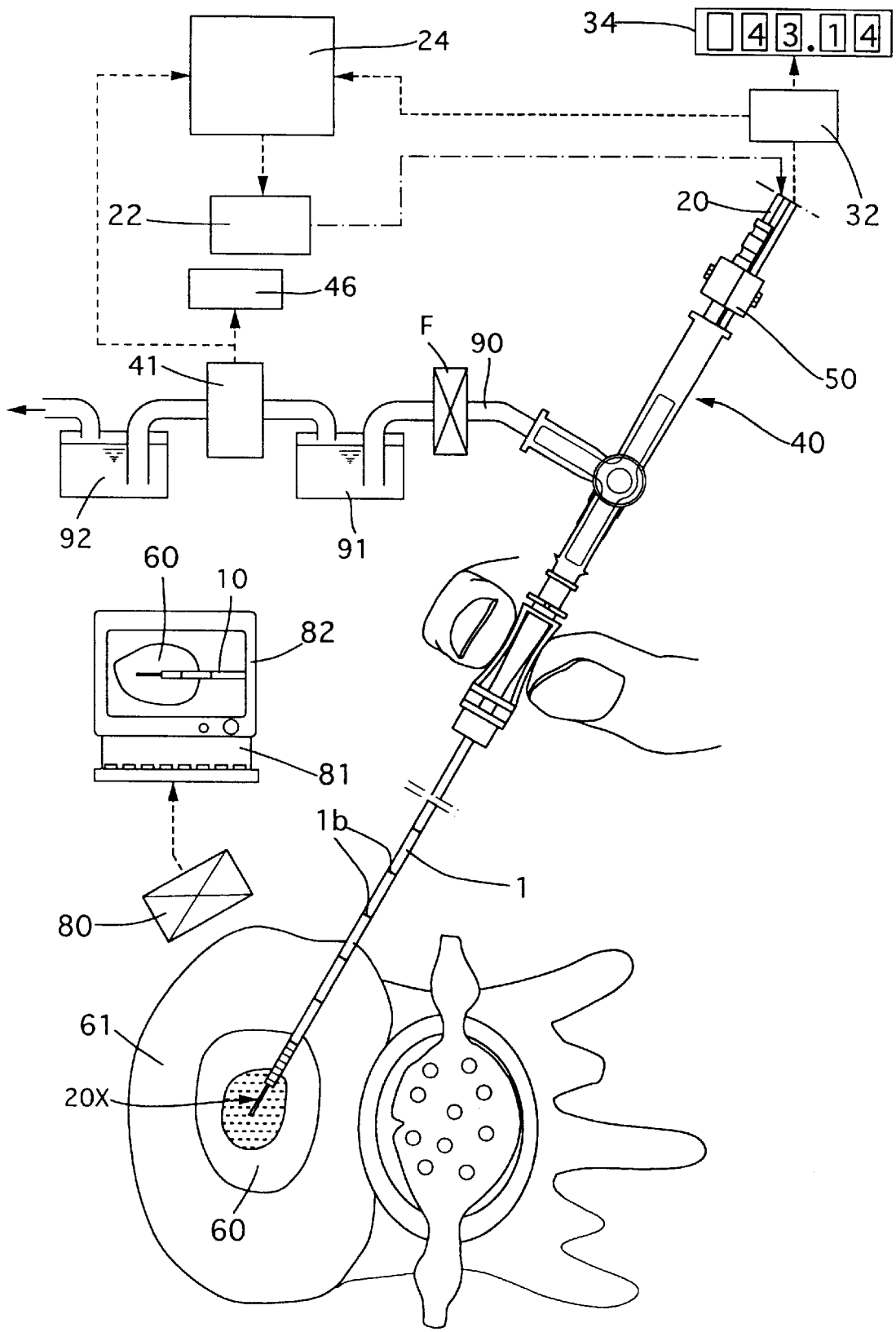
FIG. 5 is an explanatory view showing the whole of the apparatus.
Figure 6:
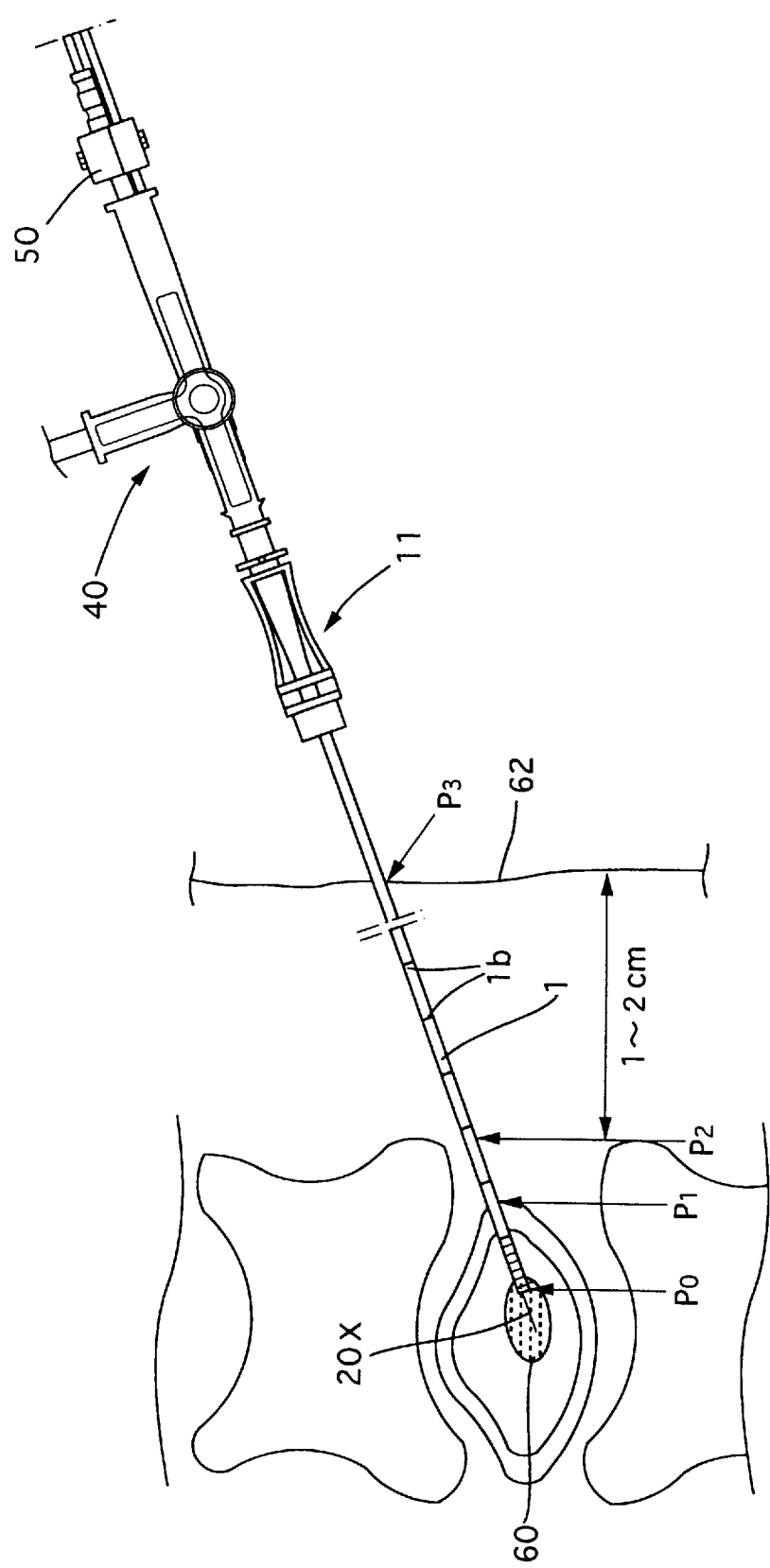
FIG. 6 is a view illustrating the treatment of the lumbar herniation disc.

FIGS. 5 and 6 show the whole of the treating apparatus and the insertion into the lumbar intervertebral disc, respectively. The apparatus will now be explained together with the treatment surgical operation procedure. The target lumbar intervertebral discs are firstly observed by MRI and the like. Both the needle member 10 and the drill member 70 are percutaneously inserted into the nucleus pulposus 60 while the drill member 70 is inserted into the needle member 10 as shown in FIG. 1. A reference numeral 61 denotes the annulus fibrosus.

Specifically, the drill wire 71 is inserted into the needle main body 1 via the knob 11 while the depressing member 72 of the drill member 70 is gripped with fingers as shown in FIG. 5. Positioning of the needle member 10 and the drill member 70 in a peripheral direction is accomplished by inserting the drill wire 71 into the needle member 10 after aligning the engaging projection 72A with the above-mentioned engaging step 2D*a* peripheral direction (FIG. 1 shows that the drill member 70 is offset by 90 degrees around the center axis thereof with respect to the needle member 10) since the engaging projection 72A enters the engaging step 2D*a* to engage therewith. Simultaneously with this, the front end face of the outer peripheral portion of the depressing member 72 will abut to the flange 11D so that positioning in a longitudinal direction is accomplished. At this insertion limit, the front end of the drill wire 71 projects beyond the front end of the needle main body 1 as shown in FIG. 4.

Under this condition, both drill member 70 and the needle member 10 are percutaneously inserted into the nucleus pulposus 60 between the lumbar intervertebral discs while the both sides 11 of the knob 11 are held by the thumb and middle finger of the right hand of the operator and the rear end of the drill member 70 is depressed by the pointing finger as mentioned above.

On insertion of the needle main body 1 no slippage of the fingers occurs since the both sides 11 of the knob 11 is concavely curved. Insertion of the needle member 10 is conducted by the operator while observing an ultrasonic image displayed by an ultrasonic diagnosis apparatus. In other words, while an ultrasonic probe 80 is brought into abutment on the body surface, the image processing is conducted by an image processor 81 based upon a resultant signal so that an image of the lumbar intervertebral disc is displayed on a CRT display 82. Since the ultrasonic waves are reflected by the needle main body 1 and more greatly reflected by the indication marks 1*b*, the operator can determine how deeply the needle main body 1 is inserted into the nucleus pulposus 60 by viewing the displayed image.

Subsequently, only the drill member 70 is removed to leave the needle member 10 within the body.

Then, the insertion portion 42a of the three-directional stopcock 40 is inserted into the knob 11 from the rear thereof until the front end face of the insertion portion 42a will abut to the receptacle hole 11AE. Then, in lieu of the drill member 70, the optical fiber 20 and the temperature detecting lead 30 are inserted into the needle main body 1 from the rear of the insertion portion 42b via the through holes 43b, 43a and the insertion portion 42a in order and then through the insertion hole 11A while holding the holder 50. Insertion is conducted until the front end face of the protective tube 33 will abut to the rear end face of the flange 44 of the insertion portion 42b.

In association of the insertion, the rigid grip member 23 is adapted into the insertion portion 42b similarly having a rigidity, which is in turn inserted into a receiving hole 11AE of the knob 11 having a rigidity, resulting in that the optical fiber 20 and the temperature detecting lead 30 are stably linked to the needle member 10 together with the holder 40. A bare portion of the temperature detecting lead 30 is inserted into the insertion hole 11AE of the knob 11 via the cut away portion of the grip member 23.

When the fiber 20 and the lead 30 reach at the insertion limit as shown in FIG. 2, the optical fiber 20 is set to such a positional relation that only scattering layer 20b projects beyond the front end face of the needle member 1. The front end face of the temperature detecting lead 30 is set to such a positional relation that it is slightly rear of the front end face of the needle member 1.

On the other hand, the discharge passage 42c is linked to the gas generation detector 41 via a discharge tube 90. It is preferable that the gas be introduced to the gas generation detector 41 after removal of dust through a filter F or trap 91 interposed therein. It is further preferable that the gas which has passed through the gas generation detector 41 be discharged to the atmosphere after absorbing the generated gas through a gas absorber 72 in which liquid such as alcohol is contained.

Under such a condition, irradiation with laser light is conducted. The laser light is preferably Nd:YAG or Ho:YAG laser since it is used for vaporizing the nucleus pulposus 60.

When the nucleus pulposus 60 is irradiated with the laser light, vaporization of the nucleus pulposus 60 occurs and the vaporized portion 60a and the solidified layer 60b are formed in such a manner as shown in FIG. 7. In other words, since the optical fiber 20 is formed at the front end portion 20X with the scattering layer 20b to make more clear the difference from the prior art of FIG. 12, the laser light is also emitted from the outer periphery of the front end portion 20X of the fiber 20 so that the vaporized portion 60a is formed around the front end portion 20X of the optical fiber 20.

As a result, the vaporized portion 60a is brought into communication with the needle member 10, specifically an opening at the front end of the needle main body 1. Accordingly, the gas which is generated by the vaporization enters the needle main body 1 from the opening at the front end thereof and passes through the insertion portion 42c of the three-directional stopcock 40 via the needle member 10 and then discharged externally of the body.

In the process of the laser light irradiation, the temperature is detected by the temperature detecting lead 30. Specifically, the detected temperature is displayed on an appropriate temperature display 34 via the thermometer 32 as shown in FIG. 5.

The gas which is generated by the vaporization of the tissue and is discharged through the needle main body 1 and the discharge tube 90 in the process of the laser light irradiation is detected by the gas generation detector 41. The flow speed or flow rate of the generated gas which is detected by this gas generation detector 41 represents the vaporization condition of the nucleus pulposus 60. The flow speed or flow rate of the generated gas which is detected by the gas generation detector 41 may be displayed on the display 46.

Accordingly, the surgical operator can manually control the necessary irradiation with the laser light by visually monitoring the flow speed or flow rate of the generated gas which is detected by the gas generation detector 41 and is displayed on the display 46. As mentioned below, the irradiation with the laser light may be automatically controlled. Mode selection between manual and automatic controls may be achieved.

Figure 8:
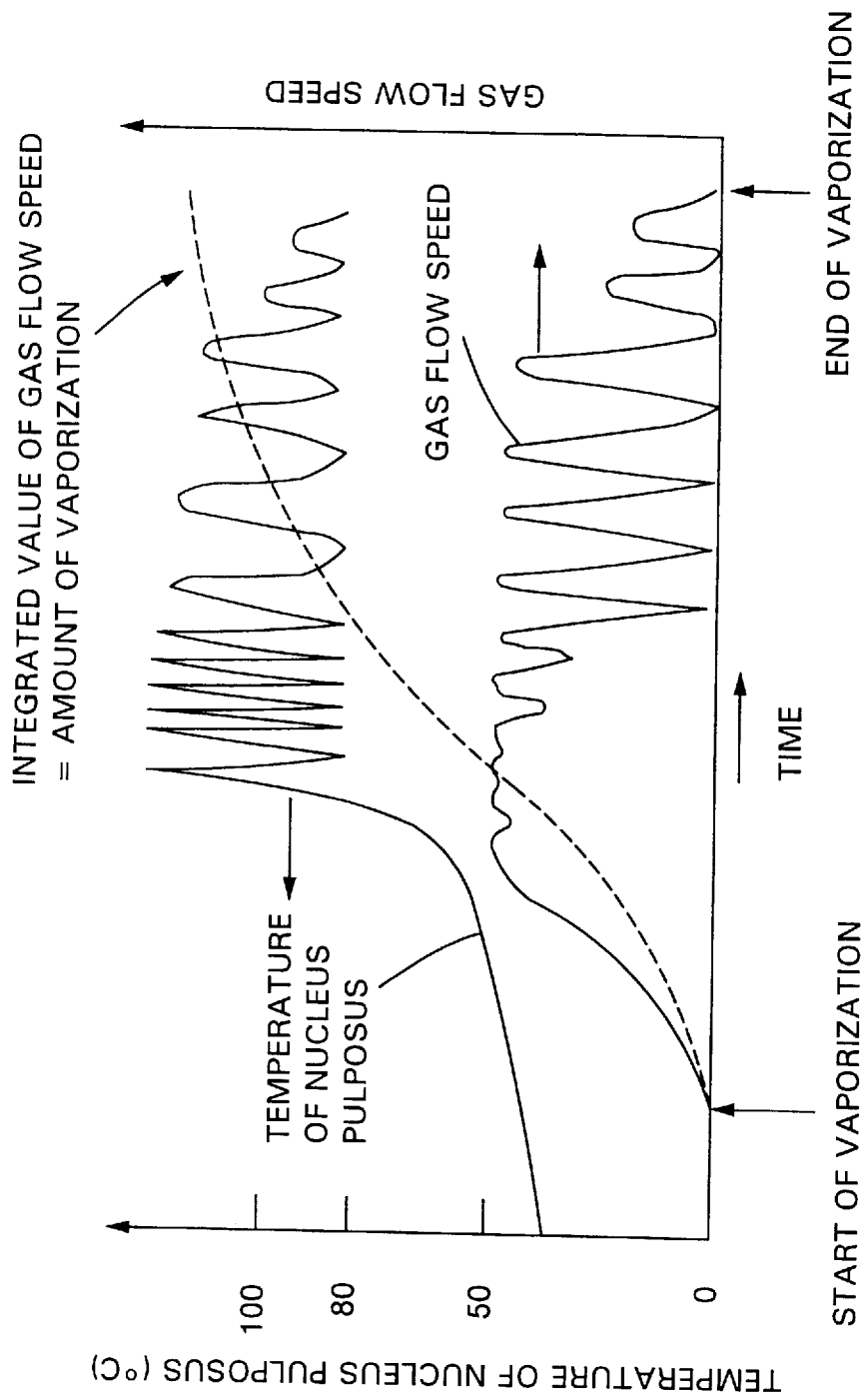
FIG. 8 is a graph showing the change with time in gas flow rate and the temperature of the nucleus pulposus.
Figure 9:
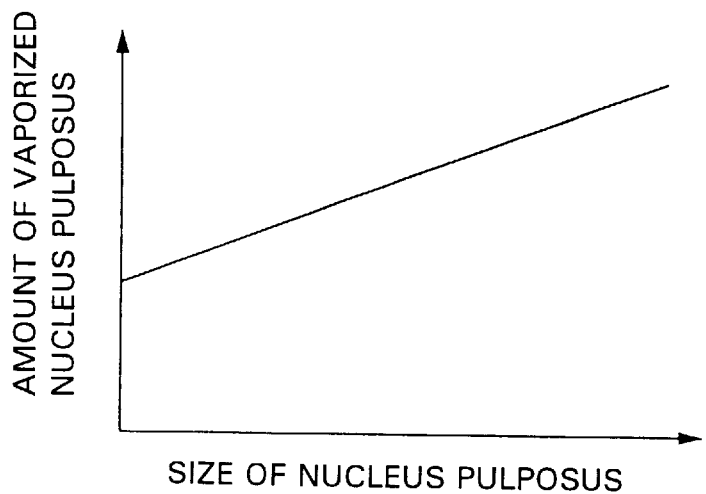
FIG. 9 is a graph showing the change in the amount of the vaporized nucleus pulposus.
Figure 10:
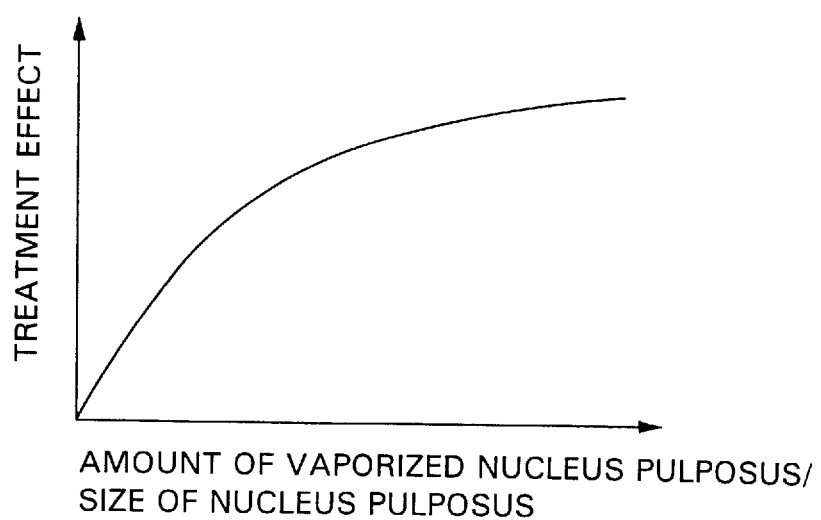
FIG. 10 is a graph showing the change in the treatment effect.
Figure 11:
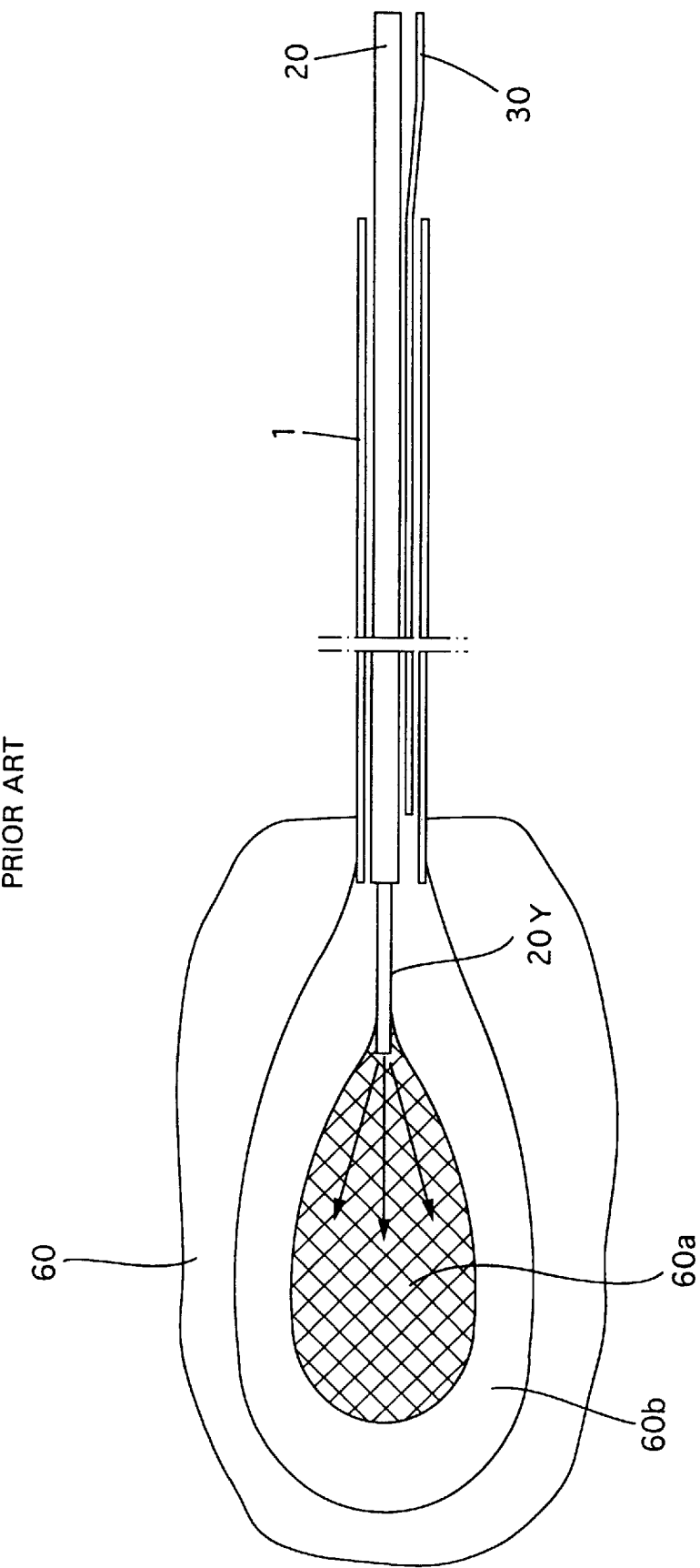
FIG. 11 is an explanatory view illustrating prior art laser light irradiation.

FIG. 8 is a graph showing the relation between the period of time of the irradiation of the nucleus pulposus with the laser light and the temperature of the nucleus pulposus and the flow speed of the discharged gas, FIG. 9 is a graph showing the relation between the size of the nucleus pulposus and the amount of vaporized nucleus pulposus, and FIG. 10 is a graph showing the relation between the amount of vaporized nucleus pulposus per size and the treatment effect. The size of the nucleus pulposus can be preliminarily determined by MRI or X-ray transmission photography.

As shown in FIG. 8, after initiation of the irradiation with the laser light is started, vaporization of the nucleus pulposus is started with the elevation of the temperature of the nucleus pulposus. The amount of vaporized nucleus pulposus increases as the temperature increases. Vaporization of the nucleus pulposus is initially large, and then exhibits a saturation tendency. The integrated value of the gas speed denotes the amount of vaporized nucleus pulposus.

If the discharge of the gas is detected by the gas generation detector 41, initiation of the vaporization of the nucleus pulposus can be determined. In case where the initiation of vaporization of the nucleus pulposus is considerably late, the laser light is not impinged, or insufficient. Thus, it can be determined that the optical fiber 20 may be damaged.

It is preferable that irradiation with the laser light be intermittently conducted at intervals of about 0.5 to 2 seconds. It is preferable to control the interval of the irradiation period of time depending upon the power of the laser light so that the temperatures in position $P_0$, at the edge of the annulus fibrosus $P_1$ in position $P_2$ between the edges of both vertebral sandwiching the target lumbar disc (1 to 2 cm below from the body skin), at position $P_3$ of the body skin 62, which are detected by the temperature detecting lead 30 are 100° C. to 80° C., 50° C. to 60° C., not higher than 45° C. and about 37° C. as shown in FIG. 6.

Feedbacking of the temperature signal which is generated by the temperature detecting lead 30 is very effective for the treatment. A patient feels insufferable heat under a local anesthesia if irradiation with the laser light is excessive. In this case, the temperature is lowered by reducing the irradiation strength of the laser light per unit time. This excessive irradiation can also be prevented by detecting the overheat of the needle main body 1. If an abnormal change in temperature occurs, it can be determined that the optical fiber 20 is damaged or the optical fiber 20 is burnt.

In this case, the system can be configured in such a manner that the surgical operator can manually control the irradiation with the laser light based upon the temperature which is detected by the thermometer 32 and displayed on the temperature display 34, or the irradiation with the laser light can be automatically controlled by controlling the laser light generator 22 or a laser transmission system including the optical fiber 20 by means of a laser light generation control 24 to which the temperature signal is applied. For example, automatic control can be achieved in such a manner that irradiation with the laser light is terminated when the detected temperature at the nucleus pulposus is elevated higher than 110° C. or the irradiation with the laser light is resumed when it is lower than 70° C.

On the other hand, the treatment effect tends to be saturated even when the nucleus pulposus is vaporized more than a given amount as shown in FIG. 10. Excessive vaporization will give an adverse influence upon the peripheral tissue of the nucleus pulposus. Therefore, an automatic control system can be configured in which the irradiation with the laser light is terminated when the amount of vaporization reaches at a predetermined value. Accordingly, a control system can be configured in which a signal representative of the gas flow rate which is detected by the gas generation detector 41 is applied to the laser light generation control 24 as shown in FIG. 5 and irradiation with the laser light is automatically terminated when the value of the gas flow rate which is integrated with time reaches at a preset value.

Since irradiation with the laser light can be appropriately achieved as mentioned above, the patient never feel heat or pain.

As mentioned above, the apparatus of the present invention can be applied to various applications such as liver tumor treatment or brain tumor treatment as well as percutaneous lumbar disc herniation treatment.

Although it is preferable to detect the temperature at the nucleus pulposus in treatment of lumbar intervertebral disc herniation, The temperature at the nucleus pulposus can be estimated based upon the temperature detected in the vicinity of the nucleus pulposus since temperature gradient can be determined from various treatments even when the temperature detection point is changed.

What is claimed is:

1. An apparatus for treating the target tissue to be treated by irradiating it with laser light for vaporizing it, characterized in that said apparatus comprises a hollow needle member which is percutaneously inserted into the target tissue;

an optical fiber for transmitting therethrough a laser light from a laser light generator to emit the laser light from the front end thereof;

a lead for detecting the temperature of said target tissue and the vicinity thereof;

means for introducing gas which is generated due to vaporization of said irradiated tissue to the outside of the body through the inside of said needle member; and generated gas detecting means for detecting the flow speed or flow rate of the gas which is generated due to the vaporization of said target tissue, and in that said optical fiber and said temperature detecting lead are inserted into said needle member from the base end thereof, said front end of said optical fiber being positioned in said target tissue;

in that the flow speed or flow rate of the gas is detected by said generated gas detecting means, the temperature of said target tissue and its vicinity being detected based upon a signal of the temperature from said temperature detecting lead; and in that the manner of irradiation with the laser light is controlled based upon the flow speed or flow rate of the detected gas and said temperature.

2. An apparatus for laser treatment as defined in claim 1 in which said optical fiber is positioned in such a manner that its front end portion projects beyond the front end of said needle member, said front end portion of said optical fiber being formed on the outer periphery thereof with light scattering means, from which the laser light emits.

3. An apparatus for laser treatment as defined in claim 2 in which said scattering means comprises a scattering layer containing finely divided particles having a refractive index less than that of the core, which is formed on the exposed core of the optical fiber at the front end thereof.

4. An apparatus for laser treatment as defined in claim 1 in which a generated gas introducing passage is provided to communicate with said needle member, said generated gas introducing passage being provided with gas detecting means.

5. An apparatus for treating the the lumbar intevertebral disc herniation by irradiating the nucleus pulposus with laser light for vaporizing it, characterized in that said apparatus comprises a hollow needle member which is percutaneously inserted into the uncleus pulposus between the lumbar discs;

an optical fiber for transmitting therethrough a laser light from a laser light generator to emit the laser light from the front end thereof;

a lead for detecting the temperature of said nucleus pulposus and the vicinity thereof;

means for introducing gas which is generated due to vaporization of said nucleus pulposus to the outside of the body through the inside of said needle member; and generated gas detecting means for detecting the flow speed or flow rate of the gas which is generated due to the vaporization of said nucleus pulposus, and in that said optical fiber and said temperature detecting lead are inserted into said needle member from the base end thereof, said front end of said optical fiber being positioned in said nucleus pulposus;

in that the flow speed or flow rate of the gas is detected by said generated gas detecting means, the temperature of said nucleus pulposus and its vicinity being detected based upon a signal of the temperature from said temperature detecting lead; and in that the manner of irradiation with the laser light is controlled based upon the flow speed or flow rate of the detected gas and said temperature.

6. An apparatus for treating the lumbar intervertebral disc herniation as defined in claim 5 in which the front end of said temperature detecting lead is positioned in the front end portion of said needle member.

7. An apparatus for treating the lumbar intervertebral disc herniation as defined in claim 5 in which said optical fiber is positioned in such a manner that its front end portion projects beyond the front end of said needle member, said front end portion of said optical fiber being formed on the outer periphery thereof with light scattering means, from which the laser light emits.

8. An apparatus for treating the lumbar intervertebral disc herniation as defined in claim 7 in which said scattering means comprises a scattering layer containing finely divided particles having a refractive index less than that of the core, which is formed on the exposed core of the optical fiber at the front end thereof.

9. An apparatus for treating the lumbar intervertebral disc herniation as defined in claim 5 in which a generated gas introducing passage is provided to communicate with said needle member, said generated gas introducing passage being provided with gas detecting means.

10. An apparatus for treating lumbar intervertebral disc herniation as defined in claim 5 and further including means for automatically controlling the irradiation with laser light based upon said detected flow speed or flow rate of gas and said detected temperature.

* * * * *